United States Patent [19]

Engelhardt et al.

[11] Patent Number: 4,603,133

[45] Date of Patent: Jul. 29, 1986

[54] AMIDES AND ESTERS OF 2-[N-(MORPHOLINOALKYL)AMINOSULFONYL]-6-NITROBENZOIC ACIDS AND COMPOSITIONS USEFUL AS ADJUNCTS TO RADIATION THERAPY

[75] Inventors: Edward L. Engelhardt, Gwynedd Valley; Walfred S. Saari, Lansdale, both of Pa.

[73] Assignee: Merck & Co., Inc., Rahway, N.J.

[21] Appl. No.: 795,565

[22] Filed: Nov. 6, 1985

[51] Int. Cl.[4] .................. A61K 31/535; C07D 295/14
[52] U.S. Cl. .................................... 514/229; 544/159
[58] Field of Search ..................... 544/159; 514/229

[56] References Cited

U.S. PATENT DOCUMENTS 4,396,622  8/1983  Jozic ................................. 544/159

Primary Examiner—Robert W. Ramsuer
Attorney, Agent, or Firm—Hesna J. Pfeiffer; Thomas E. Arther

[57] ABSTRACT

Amide and ester derivatives of 2-[N-(morpholinoalkyl)aminosulfonyl]-6-nitrobenzoic acids are disclosed to have activity in increasing the sensitivity of hypoxic tumor cells to therapeutic radiation. Also disclosed are methods of preparing such compounds and pharmaceutical compositions including such compounds.

6 Claims, No Drawings

AMIDES AND ESTERS OF 2-[N-(MORPHOLINOALKYL)AMINOSULFONYL]-6-NITROBENZOIC ACIDS AND COMPOSITIONS USEFUL AS ADJUNCTS TO RADIATION THERAPY

BACKGROUND OF THE INVENTION

This invention relates to esters, amides and N-substituted amides of 2-[N-(morpholinoalkyl)aminosulfonyl]-6-nitrobenzoic acids, used as sensitizers of hypoxic tumor cells to therapeutic radiation. It also relates to the process of preparing such compounds starting with a 2-chlorosulfonyl-6-nitrobenzoate ester prepared as described in U.S. Ser. No. 716,886 filed Mar. 27, 1985 and aminating said 2-chlorosulfonylbenzoate ester to produce the corresponding sulfamyl or N-substituted sulfamylnitrobenzoic esters.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, and are believed to have a more favorable therapeutic ratio.

DETAILED DESCRIPTION OF THE INVENTION

The compositions of the present invention are nitrobenzenesulfonamide compounds of the formula

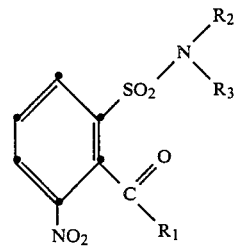

wherein
$R_1$ is hydroxy-(lower alkoxy), lower alkoxy, allyloxy, amino, monoalkylamino, dialkylamino, (hydroxyalkyl)amino, di(hydroxyalkyl)amino, or allyl amino.
$R_2$ is hydrogen, lower alkyl from 1-4 carbon atoms, hydroxy-(lower alkyl), allyl.
$R^3$ is a morpholinoalkyl radical of the formula

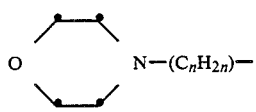

wherein n is 2 or 3.

The ester and amide derivatives of 2-[N-(morpholinoalkyl)aminosulfonyl]-6-nitrobenzoic acid, of the present invention are prepared in the following manner:

A substituted nitrobenzoate ester or nitrobenzamide having a 2-chlorosulfonyl substituent in an aprotic solvent such as tetrahydrofuran, dioxane, dimethoxyethane, or chloroform is treated with at least an equimolar amount of an amine of the formula

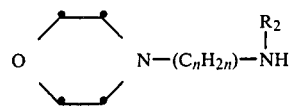

wherein n and $R_2$ are as described hereinabove.

It is preferred to carry out the reaction in the presence of a base in sufficient amount to neutralize the hydrogen chloride formed in the course of the reaction. The base utilized may be a tertiary amine such as triethylamine or pyridine. On the other hand the same results may be produced by adding at least twice the molar amount of reactant amine theoretically required. In this event, the reactant amine is utilized both to form the sulfonamide and to neutralize the hydrogen chloride formed in the amination reaction.

The temperature at which the reaction is carried out is not critical and may vary from 0°–100° C. or at the reflux temperature of the solvent, if under 100° C. The reaction temperature is preferably maintained at about 0°–25° C. for a period of 1–24 hours. The amination reaction may be formulated as follows:

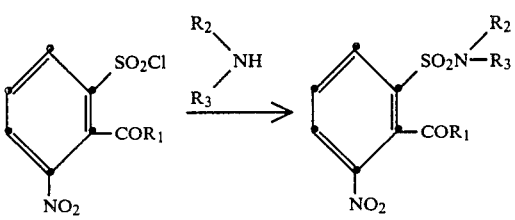

wherein $R_1$, $R_2$ and $R_3$ are as defined hereinabove.

The starting materials for the process are either known or are readily prepared from the known 2-amino-6-nitrobenzoic acid by a process of esterification followed by diazotization of the amino group and treating the formed diazonium compound with $SO_2$ in the presence of $CuCl_2$ whereby the desired starting 2-chlorosulfonyl-6-nitrobenzoate ester is formed.

The benzamide derivatives of this invention may also be prepared by reaction of a 2-(mono-substituted sulfamyl)-6-nitrobenzoate ester of formula III with ammonia or a mono- or dialkyl-substituted amine of formula IV.

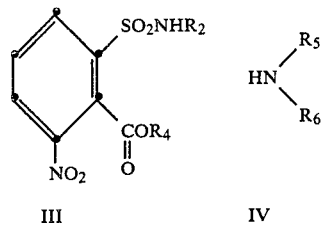

In formula III, $R_2$ is as described hereinabove and $R_4$ is either loweralkyl or hydroxyloweralkyl. In formula IV, $R_5$ and $R_6$ are each separately hydrogen, alkyl, allyl or hydroxyalkyl.

The reaction is carried out in a suitable solvent such as a lower aliphatic alcohol or a polar aprotic solvent such as dimethylformamide, dimethylsulfoxide or others such as tetrahydrofuran, glyme, diglyme, chloroform or methylenechloride. The reaction temperature is not critical and may vary from 0°–100° C., preferably from about 25°–50° C. for a period of 1 to 10 days. When low boiling amines are used, the reaction may be run in a sealed vessel.

The method of treatment of human patients or domestic animals undergoing radiation treatment of malignant disease processes employs the compounds of the present invention in pharmaceutical compositions that are administered orally or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs may also be used.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention. Temperatures are in degrees Celsius unless otherwise indicated throughout the application.

EXAMPLE 1

Methyl 2-[N-(2-Morpholinoethyl)aminosulfonyl]-6-nitrobenzoate

A solution of 4-(2-aminoethyl)morpholine (0.95 ml, 7.2 mmol) in THF (25 ml) was added over 25 minutes to a stirred, cooled solution of methyl 2-chlorosulfonyl-6-nitrobenzoate (1.0 g, 3.6 mmol) in THF (100 ml) and the reaction mixture stirred at 20°–25° C. for 20 hours. After removing THF under reduced pressure, the residue was partitioned between EtOAc and saturated Na$_2$CO$_3$ solution. The EtOAc extract was washed (saturated NaCl solution), dried (Na$_2$SO$_4$), filtered and concentrated. Flash chromatography of the residue over silica gel and elution with 1% MeOH-99% CHCl$_3$ gave 700 mg of pure product. An analytical sample, m.p. 109°–11° C., was obtained upon recrystallization from EtOAc-hexane.

EXAMPLE 2

N,N-Dimethyl 2-[N-(2-Morpholinoethyl)aminosulfonyl]-6-nitrobenzamide Hydrochloride A solution of methyl 2-[N-(2-morpholinoethyl)aminosulfonyl]-6-nitrobenzoate (0.60 g, 1.61 mmol) and 1.8 ml of a 40% aqueous dimethylamine solution in methanol (20 ml) was allowed to stand at 20°–25° C. for 3 days. After concentrating under reduced pressure, the residue was flash chromatographed over silica gel and eluted with 2% isopropyl alcohol-98% CH$_2$Cl$_2$ to give 300 mg of product. Treatment with anhydrous ethanolic hydrogen chloride and recrystallization from MeOH-EtOAc-hexane gave the HCl salt, m.p. 206°–07° C.

EXAMPLE 3

Methyl 2-[N-(3-Morpholinopropyl)aminosulfonyl]-6-nitrobenzoate

A solution of 4-(3-aminopropyl)morpholine (1.04 g, 7.2 mmol) in THF (25 ml) was added slowly to a cooled solution of methyl 2-chlorosulfonyl-6-nitrobenzoate (1.0 g, 3.6 mmol) in THF (75 ml). After stirring at 20°–25° C. for 20 hours, THF was removed under reduced pressure and the residue partitioned between EtOAc and a saturated aqueous solution of NaCl. The EtOAc extract was dried (Na$_2$SO$_4$), filtered and concentrated. Flash chromatography of the residue and elution with 2% MeOH-98% CHCl$_3$ gave 1.4 g of product as an oil.

EXAMPLE 4

N,N-Dimethyl 2-[N-(3-Morpholinopropyl)aminosulfonyl]-6-nitrobenzamide

A solution of methyl 2-[N-(3-morpholinopropyl)aminosulfonyl]-6-nitrobenzoate (1.2 g, 3.1 mmol) and 5 ml of a 40% aqueous dimethylamine solution in MeOH (50 ml) was stirred at 20°–25° C. for 4 days. After concentrating under reduced pressure, the residue was flash chromatographed over silica gel and eluted with 2% MeOH-98% CHCl$_3$ to give 300 mg of product. An analytical sample, m.p. 104°–06° C., was obtained by recrystallization from EtOAc-hexane.

What is claimed is:

1. A substituted aminosulfonyl-6-nitrobenzoic ester or amide of the formula

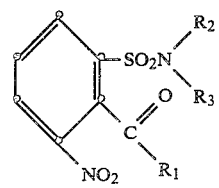

wherein
R$_1$ is alkoxy, hydroxy alkoxy, allylloxy, amino, monoalkylamino, dialkylamino, (hydroxyalkyl)amino, di(hydroxyalkylamino) or allylamino;
R$_2$ is hydrogen, alkyl, hydroxyalkyl, allyl, alkyl;
R$_3$ is a morpholinoalkyl radical of the formula

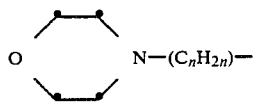

wherein n is 2 or 3.

2. The compound of claim 1 which is methyl 2-[N-(2-morpholinoethyl)aminosulfonyl]-6-nitrobenzoate.

3. The compound of claim 1 which is N,N-dimethyl 2-[N-(2-morpholinoethyl)aminosulfonyl]-6-nitrobenzamide.

4. The compound of claim 1 which is methyl 2-[N-(3-morpholinopropyl)aminosulfonyl]-6-nitrobenzoate.

5. The compound of claim 1 which is N,N-dimethyl-2-[N-(3-morpholinopropyl)aminosulfonyl]-6-nitrobenzamide.

6. A pharmaceutical composition for enhancing the therapeutic effect of radiation which consists of an effective amount of a compound defined in claim 1 and a non-toxic pharmaceutically acceptable carrier.

* * * * *